United States Patent
Barker et al.

(10) Patent No.: US 10,395,352 B2
(45) Date of Patent: Aug. 27, 2019

(54) AUTOMATIC COMPENSATION FOR THE LIGHT ATTENUATION DUE TO EPIDERMAL MELANIN IN SKIN IMAGES

(71) Applicant: Kent Imaging, Calgary (CA)

(72) Inventors: Andrew Barker, Calgary (CA); Donald Chapman, Calgary (CA); Elizabeth Dickin, Calgary (CA); Matt Cervi, Calgary (CA)

(73) Assignee: KENT IMAGING, Calgary, Alberta (CA)

( * ) Notice: Subject to any disclaimer, the term of this patent is extended or adjusted under 35 U.S.C. 154(b) by 0 days.

(21) Appl. No.: 15/574,637

(22) PCT Filed: May 18, 2016

(86) PCT No.: PCT/CA2016/050557
§ 371 (c)(1),
(2) Date: Nov. 16, 2017

(87) PCT Pub. No.: WO2016/183676
PCT Pub. Date: Nov. 24, 2016

(65) Prior Publication Data
US 2018/0137609 A1    May 17, 2018

Related U.S. Application Data

(60) Provisional application No. 62/164,261, filed on May 20, 2015.

(51) Int. Cl.
*G06T 5/00* (2006.01)
*A61B 5/103* (2006.01)
(Continued)

(52) U.S. Cl.
CPC ............ *G06T 5/009* (2013.01); *A61B 5/1032* (2013.01); *A61B 5/14551* (2013.01); *G06T 5/50* (2013.01);
(Continued)

(58) Field of Classification Search
CPC ......... G06T 5/009; G06T 7/90; G06T 7/0012; G06T 5/50; G06T 2207/20208;
(Continued)

(56) References Cited

U.S. PATENT DOCUMENTS

2009/0318908 A1    12/2009 Van Pieterson et al.
2011/0301411 A1    12/2011 Bandic et al.
(Continued)

OTHER PUBLICATIONS

Norimichi Tsumura et al: Regression-based model of skin diffuse reflectance for skin color analysis, Optical Review, Sprinder, Berlin, DE, vol. 15, No. 6, Dec. 5, 2008, pp. 292-294, XP019635640, ISSN: 1349-9432, DOI: 10.1007/S10043-008-0047-3.
(Continued)

*Primary Examiner* — John W Lee
(74) *Attorney, Agent, or Firm* — Michael R. Williams; Ryan W. Dupuis; Ade & Company Inc.

(57) ABSTRACT

Melanin is an effective absorber of light and is able to dissipate the majority of light absorbed by the pigment. This can mask the absorbance of biomolecules of interest such as hemoglobin when imaging skin tissue. Melanin is the primary determinant of skin color which can vary between individuals as well as within individuals (due to the presence of portions of skin with more or less pigment as well as features such as freckles and moles). Described herein are methods for compensating for melanin absorption at the pixel level of an image, thereby allowing for more accurate imaging of concentration and distribution of biomolecules of interest in a tissue portion.

6 Claims, 12 Drawing Sheets

(51) Int. Cl.
    *A61B 5/1455*     (2006.01)
    *G06T 5/50*       (2006.01)
    *G06T 7/00*       (2017.01)
    *G06T 7/90*       (2017.01)
    *A61B 5/00*       (2006.01)

(52) U.S. Cl.
    CPC .............. *G06T 7/0012* (2013.01); *G06T 7/90* (2017.01); *A61B 5/6824* (2013.01); *A61B 5/7203* (2013.01); *A61B 5/7264* (2013.01); *G06T 2207/10016* (2013.01); *G06T 2207/10024* (2013.01); *G06T 2207/10048* (2013.01); *G06T 2207/20208* (2013.01); *G06T 2207/20224* (2013.01); *G06T 2207/30088* (2013.01)

(58) Field of Classification Search
    CPC . G06T 2207/20224; G06T 2207/10016; G06T 2207/10024; G06T 2207/10048; G06T 2207/30088; A61B 5/1032; A61B 5/14551; A61B 5/7203; A61B 5/6824; A61B 5/7264
    See application file for complete search history.

(56) References Cited

U.S. PATENT DOCUMENTS

| | | | |
|---|---|---|---|
| 2012/0078075 A1* | 3/2012 | Maynard | A61B 5/0071 600/365 |
| 2014/0257113 A1* | 9/2014 | Panasyuk | A61B 5/0075 600/476 |
| 2014/0527113 | 9/2014 | Panasyuk et al. | |
| 2016/0022181 A1* | 1/2016 | Valsan | A61B 5/02007 600/324 |

OTHER PUBLICATIONS

Widdowson D C et al: Construction of a novel port wine stain phantom and measurement of colour by digital imaging and reflectance spectrophotometry, Lasers in Medical Science, Springer-Verlag, LO, vol. 23. No. 4, Oct. 26, 2007, pp. 369-374, XP109636564, ISSN: 1435-604X.

Seo Inseok et al: Assessing human skin with diffuse reflectance spectroscopy and colorimetry, Photonic Therapeutics and Diagnostics VII, SPIE, 100020th St. Bellingham WA 98225-6705 USA, vol. 8207, No. 1, Feb. 3, 2012, pp. 1-5 XP06002567 DOI: 10.117/12.910206.

* cited by examiner

Figure 1

| Subject | Color | L* |
|---|---|---|
| 1 | | 64.4 |
| 2 | | 65.0 |
| 3 | | 63.2 |
| 4 | | 51.8 |
| 5 | | 62.0 |
| 6 | | 60.2 |
| 7 | | 66.1 |
| 8 | | 57.6 |
| 9 | | 62.5 |
| 10 | | 61.0 |
| 11 | | 59.3 |
| 12 | | 54.0 |
| 13 | | 63.3 |
| 14 | | 54.1 |
| 15 | | 66.6 |
| 16 | | 57.2 |
| 17 | | 47.8 |
| 18 | | 63.0 |
| 19 | | 64.8 |
| 20 | | 63.9 |
| 21 | | 64.2 |
| 22 | | 58.2 |
| 23 | | 65.7 |
| 24 | | 57.9 |
| 25 | | 46.0 |
| 26 | | 66.9 |
| 27 | | 67.8 |
| 28 | | 65.9 |
| 29 | | 58.7 |
| 30 | | 63.4 |
| 31 | | 60.7 |
| 32 | | 57.3 |
| 33 | | 67.4 |
| 34 | | 64.3 |
| 35 | | 53.9 |
| 36 | | 56.2 |
| 37 | | 44.5 |
| 38 | | 44.9 |
| 39 | | 61.8 |
| 40 | | 61.2 |
| 41 | | 59.4 |
| 42 | | 59.5 |
| 43 | | 46.7 |
| 44 | | 56.2 |
| 45 | | 51.3 |
| 46 | | 57.1 |
| 47 | | 63.8 |
| 48 | | 60.1 |
| 49 | | 68.5 |
| 50 | | 57.5 |
| 51 | | 55.5 |
| 52 | | 69.4 |
| 53 | | 67.8 |
| 54 | | 33.5 |
| 55 | | 61.7 |
| 56 | | 44.7 |
| 57 | | 60.6 |
| 58 | | 45.2 |
| 59 | | 53.2 |
| 60 | | 47.7 |
| 61 | | 67.8 |
| 62 | | 67.3 |
| 63 | | 57.5 |

AUTOMATIC COMPENSATION FOR THE LIGHT ATTENUATION DUE TO EPIDERMAL MELANIN IN SKIN IMAGES

PRIOR APPLICATION INFORMATION

The instant application is a 371 of PCT application CA2916/050557, filed May 18, 2016, which claimed the benefit of U.S. Provisional Patent Application, Ser. No. 62/164,261, filed May 20, 2015, entitled 'AUTOMATIC COMPENSATION FOR THE LIGHT ATTENUATION DUE TO EPIDERMAL MELANIN IN SKIN IMAGES', the contents of which are incorporated herein by reference.

BACKGROUND OF THE INVENTION

There are a number of applications when imaging skin where one is looking for anatomical features or physiological responses independent of skin colour. The presence of epidermal melanin can mask these features or responses. For example, it is more difficult to detect non-blanchable erythema in darker skin patients [1]. Thus there is a motivation to determine the degree of light that is being absorbed and scattered by epidermal melanin and compensate for those losses of light. The state-of-the-art typically relies on an optical model of skin where the model partitions the losses of light between epidermal melanin and other skin constituents and structures [2].

Skin has a complex structure that varies depending on anatomical location, age, health, environmental exposure and ethnicity. Developing an omnibus optical model of skin that is able to capture the complexity and diversity of skin anatomy is a serious challenge. Typically skin is modelled as a multi-layered system with each layer being optically homogeneous [3]. The accuracy of the optical properties for the individual layers is questionable as they are usually derived from a limited set of reference samples often measured under conditions that do not represent the in-vivo state of skin. Based on these limited models, light propagation in skin can be approximated using Monte Carlo simulation methods [3] or solutions to the radiative transport equation [4, 5]. In practice the inverse problem needs to be solved. The inverse model uses the measured light losses from skin as inputs to the model that partitions the losses between melanin and the constituents of skin that are of interest. Solving the inverse problem with the appropriate optical model provides estimates of the presence and concentration of constituents in skin independent of the melanin concentration. However, the structure of the underlying skin and the optical properties of these structures in the in-vivo state need to be known and incorporated into the optical model in order for the method to accurately predict the propagation of light within the target tissue.

SUMMARY OF THE INVENTION

According to a first aspect of the invention, there is provided a method of correcting a near-infrared and/or visible image of a tissue portion to correct for absorption by melanin comprising: determining skin color of the tissue portion; determining a melanin correction factor from the skin color; and correcting for melanin absorption at each wavelength used for imaging the tissue portion using the melanin correction factor.

The correction for melanin absorption may comprise multiplying absorption at each wavelength used for imaging the tissue portion by the melanin correction factor and subtracting this from said absorption at each wavelength.

The subtraction from the image may be made at pixels of the image.

The skin color may be determined by measuring light reflected from the tissue portion at two or more wavelengths and using reflectance to calculate the skin color of the tissue portion. A regression model derived from a database of reflectance measurements from subjects with known skin color or skin melanin content may be used. Similarly differences in reflectance for target skin/tissue from such database of measures where subjects have minimal and/or high melanin content can be used to estimate melanin content of the target skin/tissue.

Alternatively, the skin color may be determined using a calibrated colorimeter on the tissue portion or estimated from a color digital image of the tissue portion.

The skin color may be converted to a value corresponding to L* component of Lab color space data.

BRIEF DESCRIPTION OF THE DRAWINGS

FIG. 2: RGB representations of the in L*a*b colorimeter measurements of the skin tones of all 63 subjects used to evaluate the efficacy of our L* guided melanin correction.

FIG. 11: Oxygenation images of a forearm calculated from measuring the reflectance from skin at 670, 735, 890 and 940 nm. The forearm was imaged in a condition of normal blood flow (1st column), restricted blood flow (ischemia, $2^{nd}$ column) and where normal blood flow was restored (reperfusion, $3^{rd}$ column). The first row displays the calculated oxygenation images obtained when skin reflectance is used without accounting for melanin. The second row uses the L* guided method that requires prior knowledge of the lightness of the skin (the L* value in the Lab colorspace) to correct for the melanin content of skin prior to calculating the oxygenation image. The third row uses an estimate of skin lightness obtained directly from near infrared measurements of reflectance to correct for the melanin content of skin prior to calculating the oxygenation image. The latter method requires no prior information about the lightness of skin and the melanin correction can be performed on a pixel by pixel basis.

FIG. 12: Oxygenation images of a forearm calculated from measuring the reflectance from skin at 670, 735, 890 and 940 nm. The forearm was imaged in a condition of normal blood flow (1st column), restricted blood flow (ischemia, $2^{nd}$ column) and where normal blood flow was restored (reperfusion, $3^{rd}$ column). The first row displays the calculated oxygenation images obtained when skin reflectance is used without accounting for melanin. The second row uses an estimate of skin lightness obtained directly from near infrared measurements of reflectance to correct for the melanin content of skin prior to calculating the oxygenation image. The third row subtracts reflectance variations not related to melanin prior to calculating the melanin correction. The latter method requires prior information or a guess about the non-melanin sources of light reflectance, it projects these images onto a subspace that excludes these variations and performs a melanin correction. Note that this latter method better preserves the oxygenation contrast between the ischemia (low oxygenation) and higher oxygenation states of the forearm.

DESCRIPTION OF THE PREFERRED EMBODIMENTS

Unless defined otherwise, all technical and scientific terms used herein have the same meaning as commonly understood by one of ordinary skill in the art to which the invention belongs. Although any methods and materials similar or equivalent to those described herein can be used in the practice or testing of the present invention, the preferred methods and materials are now described. All publications mentioned hereunder are incorporated herein by reference.

Described herein is a method of imaging skin tissue wherein absorption due to melanin is corrected for in the image. Examples of imaging methods and devices that can incorporate this correction include but are by no means limited to U.S. Pat. Nos. 6,587,701; 7,289,866; 7,729,747; 7,860,554; and 8,060,188 which are incorporated herein by reference in their entirety as well as specifically for their disclosure and teaching relating to the imaging of biomolecules in vivo.

Melanin is an effective absorber of light and is able to dissipate the majority of light absorbed by the pigment. As discussed above, this can mask the absorbance of biomolecules of interest such as hemoglobin when imaging skin tissue. Correction for the absorption by melanin is complicated by a number of factors, as discussed herein. Specifically, melanin is the primary determinant of skin color which can vary between individuals as well as within individuals (due to the presence of portions of skin with more or less pigment as well as features such as freckles and moles).

Described herein are methods for compensating for melanin absorption at the pixel level of an image, thereby allowing for more accurate imaging of concentration and distribution of biomolecules of interest in a tissue portion.

In one embodiment, the amount of melanin is measured by measuring light reflected from the target tissue at two or more wavelengths and using reflectance to calculate the lightness of the skin of the tissue portion.

In other embodiments, discussed below, the lightness of the tissue portion is either known or is derived by other means.

Furthermore, as discussed below, in certain embodiments, the method is invariant to illumination because the melanin correction is based on one or more reflectance ratios. In this form the method is operative when the target tissue is partially shadowed or the tissue surface is curved.

Direct inclusion or through imputation of reflectance changes not due to melanin into the database allows for further refinement of the regression model to make it less susceptible to the influences of covariates, thereby providing more reliable melanin corrections. Covariates include the effects of temperature, topical agents and exercise which influence the superficial circulation to the skin and modify its reflectance properties. External environmental, intrinsic metabolic or physiological factors that impact cutaneous circulation, modify skin hydration or induce swelling may also be taken into account.

As discussed below, there is provided a method of correcting a near-infrared and/or visible image of a tissue portion to correct for absorption by melanin comprising:
    determining skin color of the tissue portion;
    determining a melanin correction factor from the skin color; and
    correcting for melanin absorption at each wavelength used for imaging the tissue portion using the melanin correction factor.

As discussed below, in some embodiments, the correction for melanin absorption comprises multiplying absorption at each wavelength used for imaging the tissue portion by the melanin correction factor and subtracting this from the absorption at each wavelength. This correction may be applied at pixels of the image, for example, a majority of the pixels of the image relating to the tissue portion that is being imaged, or substantially all of the pixels of the image or all of the pixels of the image relating to the tissue portion that is being imaged.

As will be appreciated by one of skill in the art, the melanin content of the skin is determined by determining the skin color or a skin color value. As discussed below, this provides a correction factor which is combined with the absorption at specific wavelengths being used for imaging. This provides a correction which can be used to effectively subtract the absorption due to melanin from any image, thereby allowing imaging of the tissue portion and particularly the biomolecules of interest within the tissue to be imaged, thereby providing information on their distribution.

In some embodiments, the skin color or skin color value is determined by measuring light reflected from the tissue portion at two or more wavelengths and using reflectance to calculate the skin color or skin color value of the tissue portion and the skin color is calculated by a regression model derived from a database of reflectance measurements from subjects with known skin color or skin melanin content, as discussed below.

In other embodiments, the skin color is determined using a calibrated colorimeter on the tissue portion or the skin color is estimated from a color digital image of the tissue portion.

As discussed herein, the skin color may be converted to a value corresponding to L* component of Lab color space data.

Described herein is a method to correct for the light attenuated by epidermal melanin when there is available a measurement of the color of the skin. This color measurement could be from a calibrated colorimeter, rendered from skin reflectance measurements of the skin or estimated from a color digital picture of the skin. From these known measurement methods an estimate of skin color can be provided in the CIELAB color space [6], also known as Lab color space. Herein, in some embodiments the L* component (lightness) of the L a b color space data is associated with the melanin content of the skin.

Specifically, as discussed in greater detail below, the attenuation of light due to the presence of epidermal melanin can be taken into account by measuring the light reflected from the target tissue at two or more wavelengths and using a regression model that relates tissue reflectance to the L* color of the target. The regression model is derived from a database of reflectance measurements from subjects with varying skin melanin content.

When the color of the target is known and can be converted to its L* value, the correction can be applied directly without resorting to the regression model derived from the data base.

For each subject, the L* value of the subject is divided by the L* value that is consistent with the lightest-skinned subjects ($L^*_{max}$=70). This ratio is subtracted from one in order to arrange the correction to have a range from 1 (darkest possible skin) to 0 (as light as the lightest subject). This was used as an estimate of the magnitude of the melanin correction. Specifically, no correction is applied to the reflectance measured from the lightest-skinned subjects and the darkest-skinned subjects (low L* values) would require the most correction.

$$M_n = 1 - \frac{L^*_n}{L^*_{max}} \quad (1.)$$

where $L^*_{max}$ is the lightest skin tone being measured. Thus, for the lightest skinned individual, the magnitude of melanin correction would be (1−70/70)=0, while for a very dark skinned individual, the magnitude of melanin correction would approach 1. In our test set the greatest M value was (1−7/70)=0.9

Figure 1:
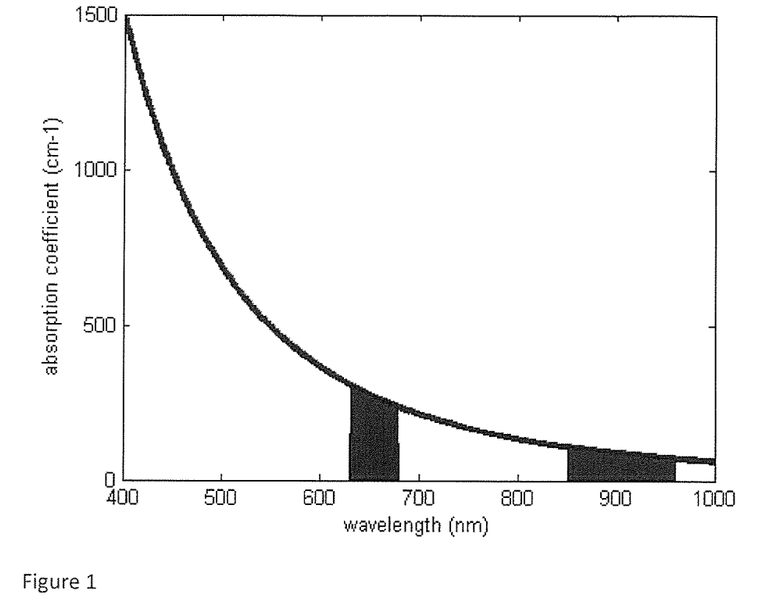
FIG. 1: The wavelength dependence of the light absorption by melanin. Over a narrow wavelength range decreases approximately linearly with increasing wavelength.

Light absorption by melanin as a function of wavelength (λ) is often modelled by equation 2 (see reference 1) and is depicted graphically in FIG. 1.

$$\mu_a^{melanin}(\lambda)=1.70\cdot10^{12}\cdot\lambda^{-3.48} \quad (2.)$$

The wavelength dependence of the correction factor is derived from this functional form for the light absorption coefficient for melanin (see equation 2) divided by the value of the melanin absorption coefficient at the maximum wavelength measured by the measurement system. Preferably the maximum wavelength exceeds 800 nm and is less than 950 nm. If the correction is to be applied over a narrow wavelength range (see for example the shaded areas in FIG. 1) a linear approximation to equation 3 can be used to obtain an adequate correction.

$$C(\lambda) = \frac{\mu_a^{melanin}(\lambda)}{\mu_a^{melanin}(\lambda_{max})} \quad (3.)$$

The overall correction factor, $F_n(\lambda)$ is given by a combination of equations (1) and (3) as presented in equation 4 where f and k are empirical constants that depend on the scale used to represent the intrinsic absorption of melanin. For the inverse centimeter scale shown in FIG. 1, adequate melanin corrections were obtained using k between 2 and 4 with f usually fixed at 10. However, these constants vary depending on the scale and the functional form used for the melanin absorption coefficient.

$$F_n(\lambda)=f\times M_n^k\times C(\lambda) \quad (4.)$$

Multiplying the measured reflectance at wavelength, A, by 1+$F_n(\lambda)$ provides a reflectance corrected for the attenuation of light due to melanin from the prior knowledge of the L* value for the skin being measured.

Validation of the L* Guided Approach

Approximately sixty (63) subjects of varying skin tones were evaluated to verify the approach outlined above. The Fitzpatrick skin type classification was used to assign each subject into one of six skin types [7]. The Fitzpatrick survey is used by practitioners when determining the skin's reaction to treatments or their chances of developing skin cancer. In this case, this survey was used as a tool to quickly assess skin colour and enroll them into the study. The Fitzpatrick skin type is designated as belonging to type I, II, III, IV, V or VI (see definition below).

Type I—Light to pale white skin
Type II—White/Fair
Type III—Medium, white to olive
Type IV—Olive, moderate brown
Type V—Brown, dark Brown
Type VI—Black, very dark brown to Black Approximately 30 subjects with skin types I to III and 30 subjects with skin types IV to VI were recruited. A calibrated hand-held colorimeter (Chroma Meter™ model CR-300) was used to measure skin color from an 8 mm diameter area of the volar forearm. The colorimeter reports the color of the target area in CIE (Commission Internationale d'Eclairage) standard units after averaging three readings from the target area. The CIE standard reports color in Lab notation where L* represents luminance or brightness, a describes where the color ranges between red and green, and b describes the range of the color between yellow and blue. The guidelines for measurement of skin colour reported by the European Society of Contact Dermatitis were followed in this protocol [8]. To visually assess the colorimeter recordings, the Lab values were converted to the RGB color space and projected on a monitor for the operator to compare to the skin tone of the subject. The palette of skin tones recorded by the colorimeter converted to the RGB color space is presented in FIG. 2.

Visible and near infrared light reflected from the skin was measured with a KC-103 multispectral imaging system from Kent Imaging. This system computes the ratio of oxygenated to deoxygenated hemoglobin at each pixel of the image and provides an oxygen saturation image of the target tissue. Light attenuation by melanin confounds these measures of oxygen saturation. Raw reflectance images collected by the KC-103 as well as images corrected using the approach described above were compared with the forearm in a comfortable resting position, when blood flow to the forearm was briefly occluded (condition known as ischemic) and immediately upon re-establishing blood-flow to the forearm (post-ischemia or reperfusion). This comparison was carried out to ensure that the melanin correction was invariant to the blood perfusion of the tissue.

Figure 3:
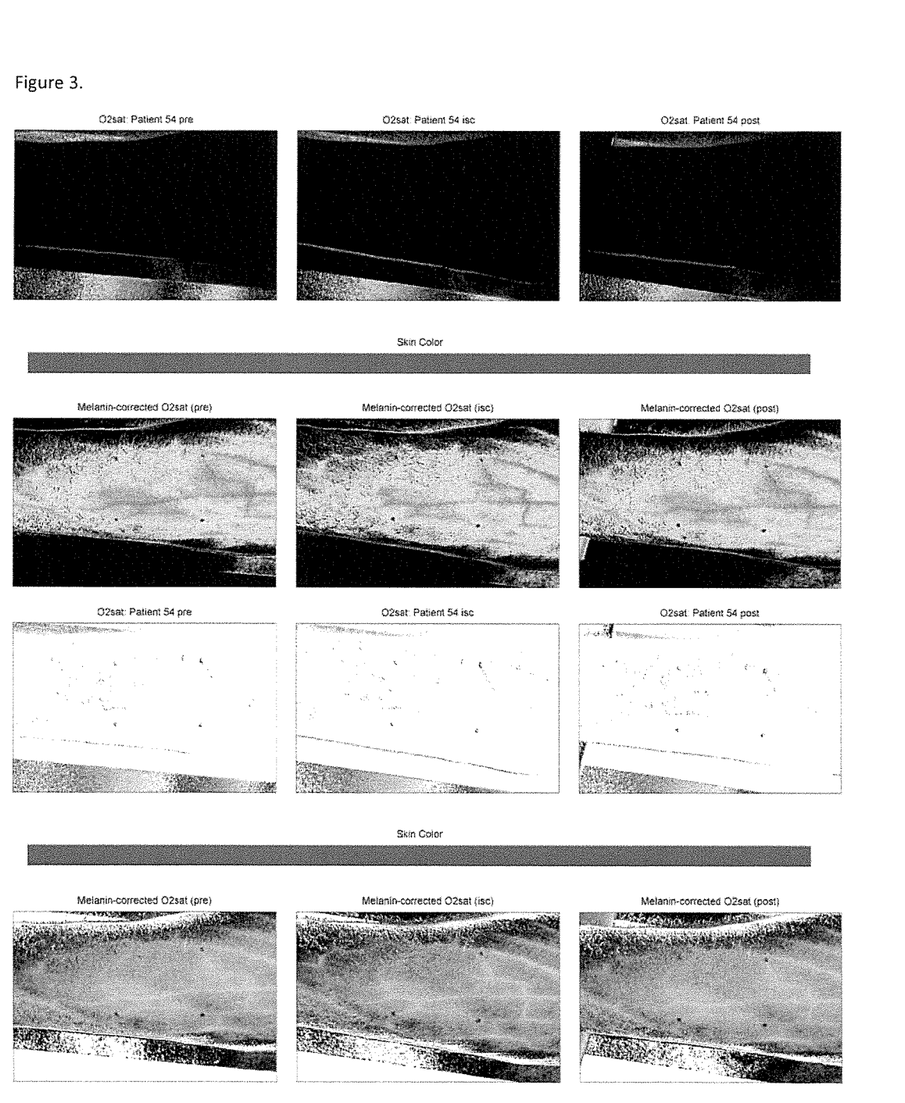
FIG. 3: Results from subject 54 the lowest L* skin reflectance measured in our cohort of subjects. Top panel: the computed hemoglobin oxygen saturation image from the uncorrected reflectance images of the volar forearm. Light attenuation by melanin overwhelms the light losses to the other absorbing molecules in the skin. Bottom panel: following correction the hemoglobin absorptions can be detected rendering a useful hemoglobin oxygen saturation image of the forearm.

Results from subject 54 that had an L* value of 33.5 at the volar forearm are shown in FIG. 3. This was the test subject with the lowest L* value. The top panel shows the computed hemoglobin oxygen saturation image from the uncorrected reflectance images of the volar forearm. As can be seen, light attenuation by melanin overwhelms the light losses to the other absorbing molecules in the skin. The bottom panel shows how following correction the hemoglobin absorptions can be detected rendering a useful hemoglobin oxygen saturation image of the forearm that was not visible previously.

Figure 4:
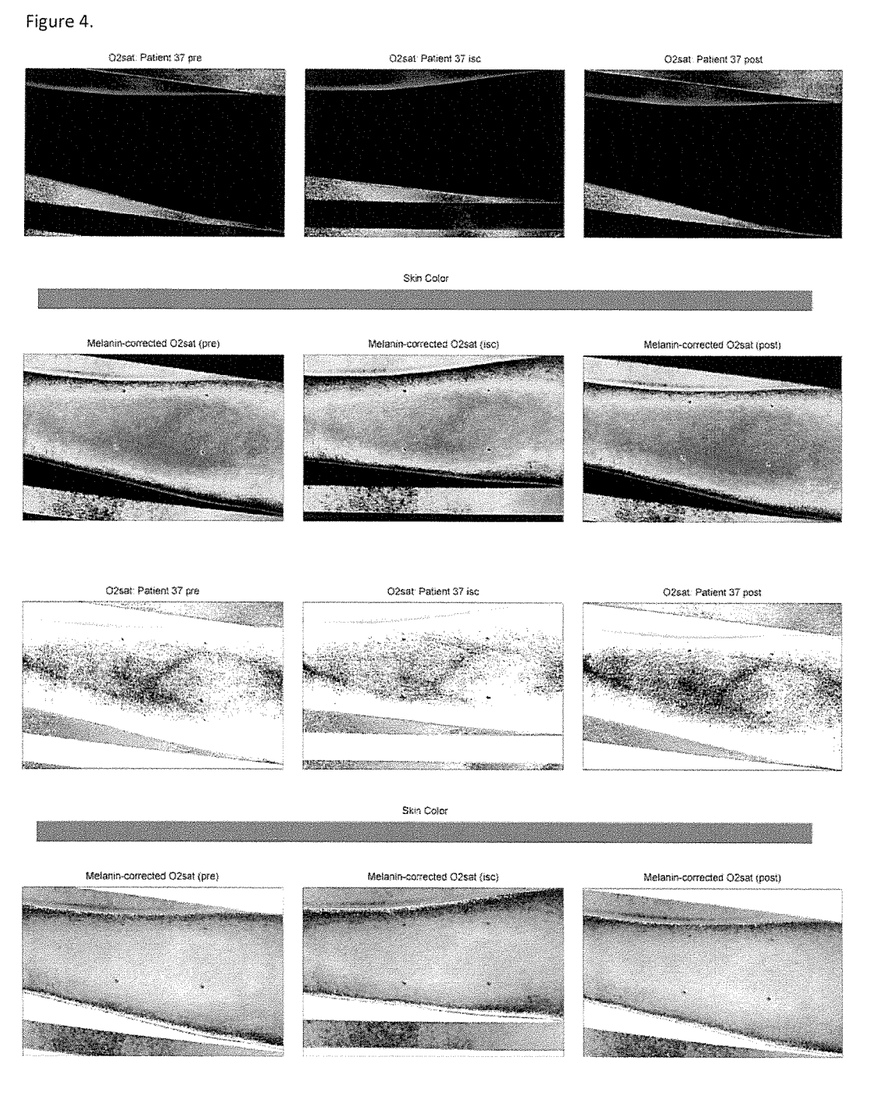
FIG. 4: Results from subject 37 another example of a subject with lower L* skin reflectance. Top panel: the computed hemoglobin oxygen saturation image from the uncorrected reflectance images of the volar forearm. Light attenuation by melanin overwhelms the light losses to the other absorbing molecules in the skin. Bottom panel: following correction the hemoglobin absorptions can be detected rendering a useful hemoglobin oxygen saturation image of the forearm.

FIG. 4 shows results from subject 37, L*=44.5. Top panel: the computed hemoglobin oxygen saturation image from the uncorrected reflectance images of the volar forearm. Light attenuation by melanin overwhelms the light losses to the other absorbing molecules in the skin. Bottom panel: following correction the hemoglobin absorptions can be detected rendering a useful hemoglobin oxygen saturation image of the forearm.

Figure 5:
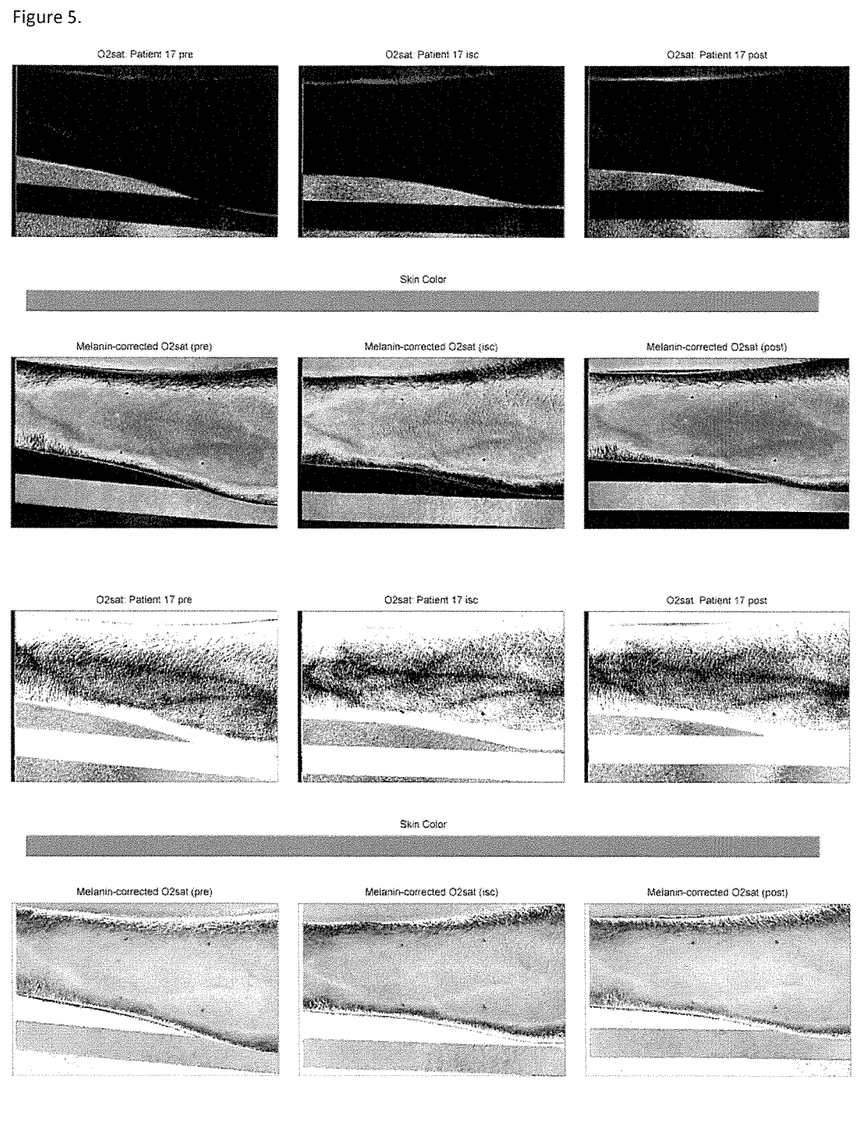
FIG. 5: Results from subject 17, another subject with low L* reflectivity. Top panel: the computed hemoglobin oxygen saturation image from the uncorrected reflectance images of the volar forearm. Bottom panel: following correction the hemoglobin absorptions can be detected rendering a useful hemoglobin oxygen saturation image of the forearm.

FIG. 5 show results from another subject (subject 17) with a relatively low lightness parameter, L*=47.8. Top panel: the computed hemoglobin oxygen saturation image from the uncorrected reflectance images of the volar forearm. Light attenuation by melanin overwhelms the light losses to the other absorbing molecules in the skin. Bottom panel: following correction the hemoglobin absorptions can be detected rendering a useful hemoglobin oxygen saturation image of the forearm.

Figure 6:
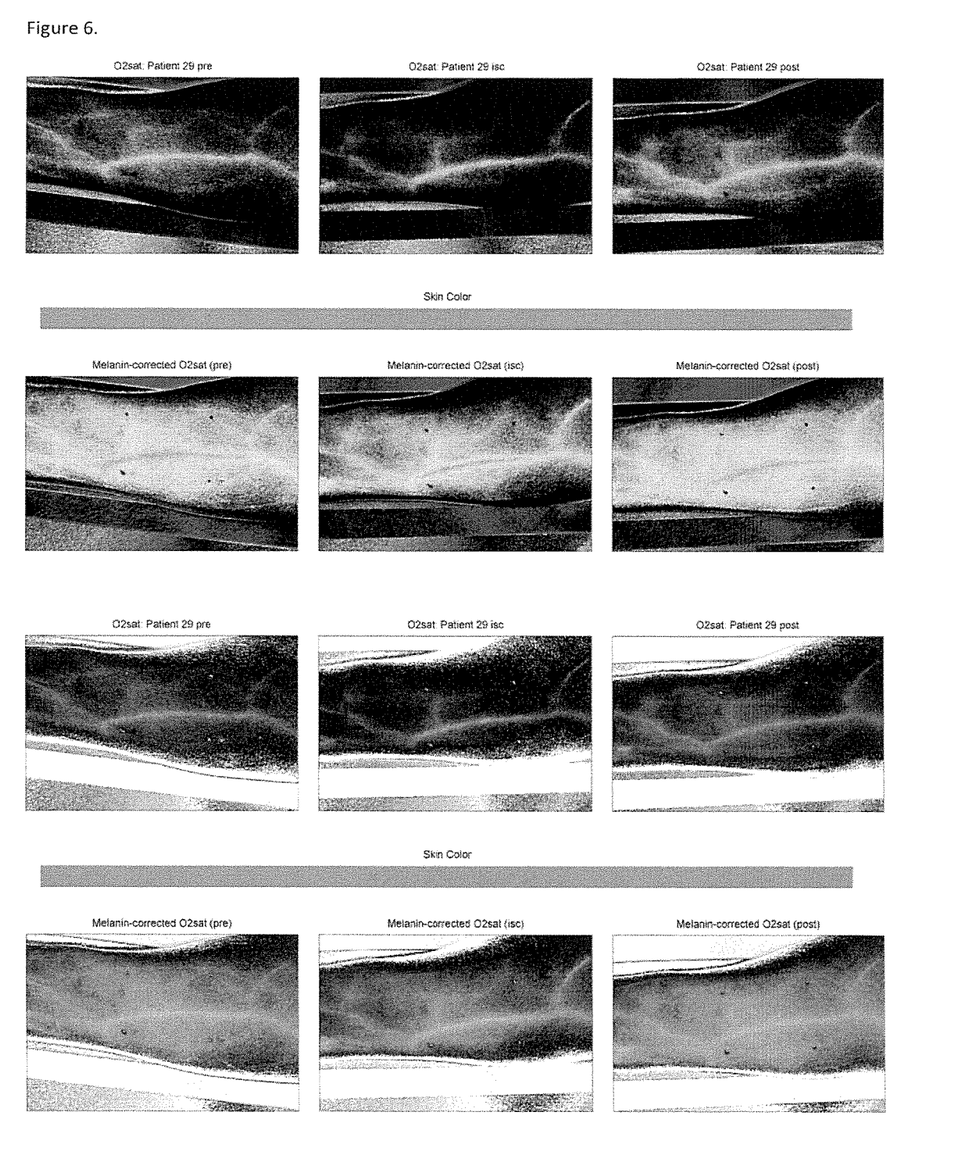
FIG. 6: Results from subject 29 (mean L* value). Top panel: the computed hemoglobin oxygen saturation image from the uncorrected reflectance images of the volar forearm. Although this subject has a higher L* value for skin reflectance compared to the earlier examples, light losses due to melanin are still significant and confound the calculation of an oxygenation saturation value from the near infrared reflectance images. Bottom panel: following correction for the light losses due to melanin the hemoglobin absorptions can be detected rendering a useful hemoglobin oxygen saturation image of the forearm.

FIG. 6 shows results from subject 29 (mean L* value), L*=58.7. Top panel: the computed hemoglobin oxygen saturation image from the uncorrected reflectance images of the volar forearm. The skin has a higher lightness but light attenuation by melanin is an important contributor in light losses in the measured light reflectance. Bottom panel: following correction the hemoglobin absorptions can be detected rendering a useful hemoglobin oxygen saturation image of the forearm.

Figure 7:
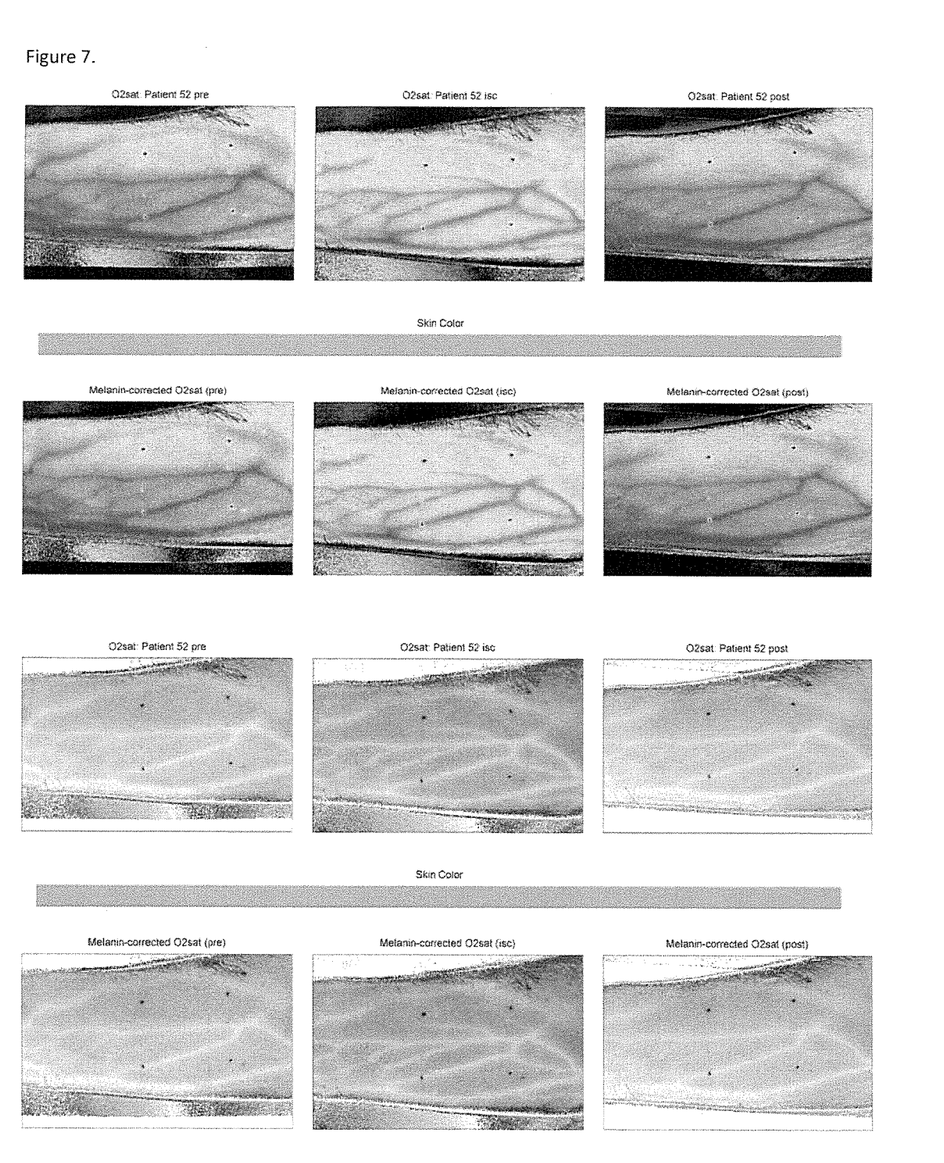
FIG. 7: Results from subject 52 (lightest skin tone). Top panel: the computed hemoglobin oxygen saturation image from the uncorrected reflectance images of the volar forearm. Light attenuation by melanin is a minor contributor and little or no correction is needed to get a useful oxygen saturation image. Bottom panel: shows the hemoglobin oxygen saturation image of the forearm after using the melanin correction algorithm.

FIG. 7 shows results from subject 52 (lightest skin tone), L*=69.4. Top panel: the computed hemoglobin oxygen saturation image from the uncorrected reflectance images of the volar forearm. Light attenuation by melanin is not significant in this case and good oxygenation images can be obtained without the need for correction. Bottom panel: the correction has only a minor effect on the hemoglobin oxygen saturation image of the forearm when skin has a light tone (high L* value).

Figure 8:
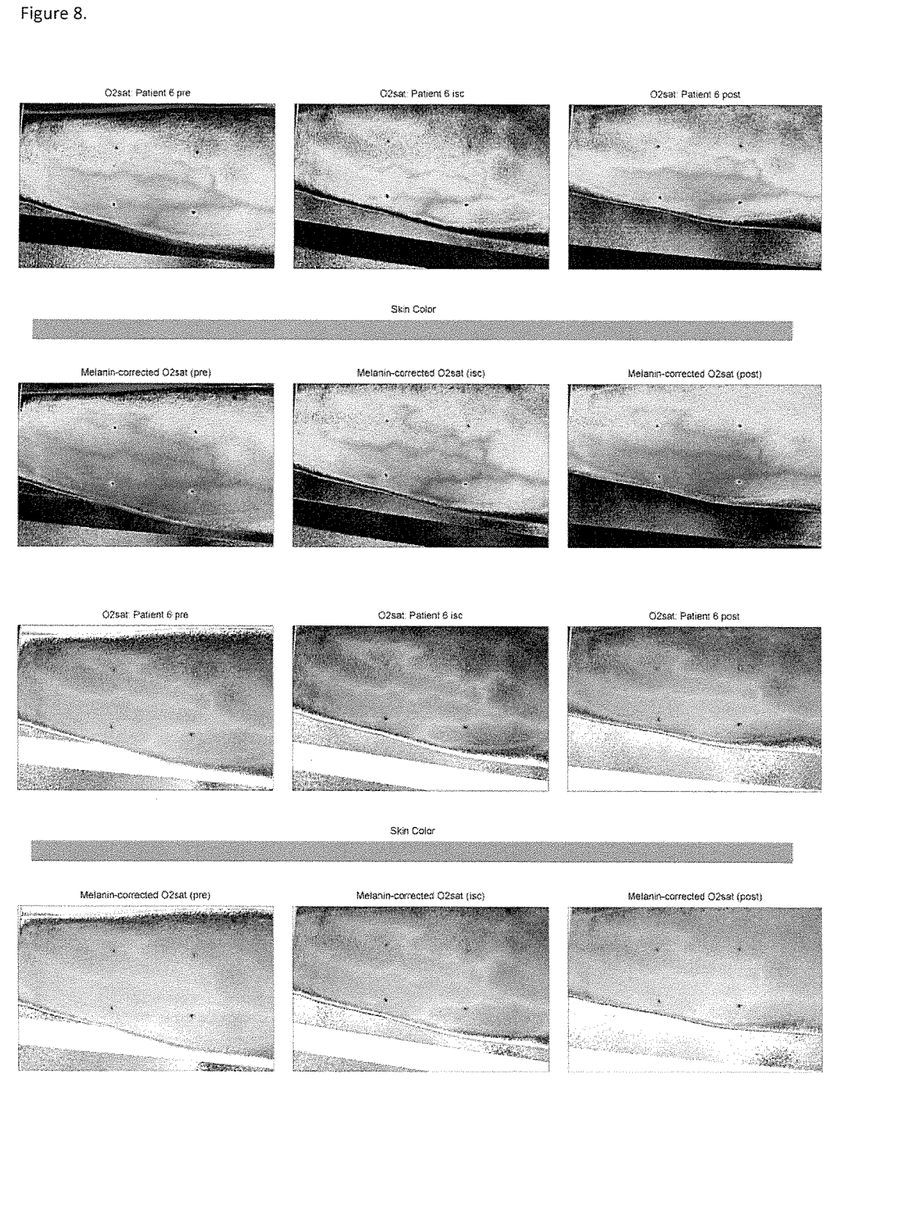
FIG. 8: Results from subject 6 (median L* value). Top panel: the computed hemoglobin oxygen saturation image from the uncorrected reflectance images of the volar forearm. This subject has a relatively high L* skin reflectance. Melanin is only a minor contributor to the light losses measured by reflectance and useful oxygenation images can be obtained with little or no melanin correction. Bottom panel: following melanin correction the hemoglobin absorptions are more readily detected rendering on average a higher hemoglobin oxygen saturation value for the forearm compared to the calculation based on the uncorrected reflectance.

FIG. 8 shows results from subject 6 (median L* value), L*=60.2. Top panel: the computed hemoglobin oxygen saturation image from the uncorrected reflectance images of the volar forearm. Light attenuation by melanin has a small masking effect on detecting the light losses arising from other absorbing molecules in the skin. Bottom panel: following correction the hemoglobin absorptions can be detected rendering a useful hemoglobin oxygen saturation image of the forearm.

Also described is a method to compensate for the light losses due to epidermal melanin that borrows some of the concepts used in the L* guided melanin correction approach but has the advantage that prior knowledge of the underlying structure or optical properties of the skin or measurement of the skin color (L*) is not needed. The method compensates for the light attenuation due to melanin at the pixel level. Thus it is able to deal with scenes with inhomogeneous pigmentation. The method has the added advantage in that it can be made to be invariant to illumination. Thus it is still operative over partially shadowed areas or curved surfaces.

The method relies on acquiring two or more images of the same scene at different wavelengths in the visible and/or near-infrared, (400-1000 nm). Wavelength regions where there is a large difference in the light absorption by melanin but a small differential light absorption by other skin constituents are optimal regions to select in order to effectively compensate for light absorption due to melanin. Using the data acquired from subjects recruited for establishing the L* guided method, a multilinear regression model is developed to relate the reflectance measured at a series of wavelengths to the L* value measured for the subjects or used to directly predict the correction factor M given in equation (1). The regression model is constrained to minimize the co-variance due to varying hemoglobin and other molecular constituents of skin by careful selection or weighting of wavelengths used in the regression model. Reflectance measured at nearby wavelengths is generally highly correlated. Thus it is not uncommon to have collinear data motivating the need to impose a regularization term in the regression model or adopt a reduced rank latent variable model such as principal components analysis or partial least squares. Using the database that established the L* guided method, a robust regression model is developed to predict the melanin correction factor (see equation 1) for subject I from the reflectance ($\lambda$) measured at K different wavelengths.

$$M_i = \beta_0 + \sum_{j=1}^{K} \beta_j \lambda_{i,j} \tag{5}$$

Equation 6 discloses one illumination invariant version of the melanin correction where the regression model is built on a series of reflectance ratios.

$$M_i = \beta_0 + \sum_{j=1}^{K} \beta_j \tilde{\lambda}_{i,j} \text{ where} \tag{6}$$

$$\tilde{\lambda}_{i,j} = \frac{\lambda_{i,j}}{\sum_{j=1}^{K} \lambda_{i,j}}$$

Figure 9:
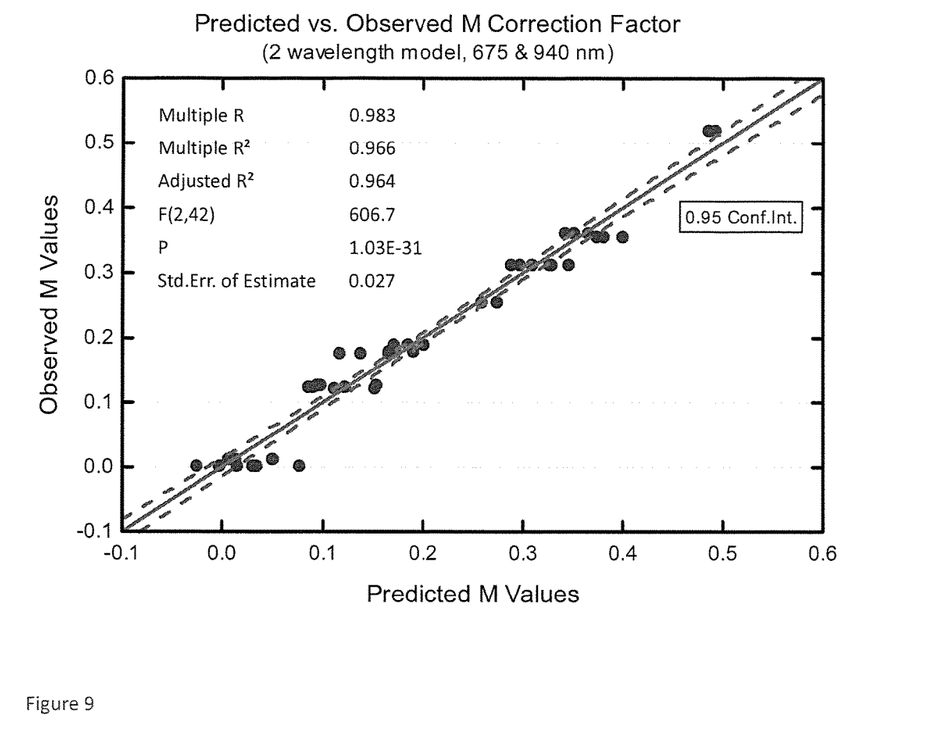
FIG. 9: Multilinear regression of the normalized light reflectance at 675 and 940 nm to predict the melanin conversion factor M=(1−L/Lmax) where L is the measured skin lightness (L*) in the Lab colorspace and Lmax is maximum value of L* (lightness) for human skin.

For example, an illumination invariant model based on measuring the reflectance at two wavelengths, 675 and 940 nm, provides standard error of estimate of M of 0.036 with a correlation coefficient, $R^2=0.96$ (see FIG. 9). Better fits can be obtained by measuring the reflectance at additional wavelengths. Similar corrections can be established by fitting the difference in the light reflected at two or more wavelengths from tissue of a target subject from matched reflectance measurements prototypical of tissue with limited and/or extensive melanin. These difference highlight either the melanin or the non-melanin contributions to the measured reflected light depending on the prototype tissue used.

Figure 10:
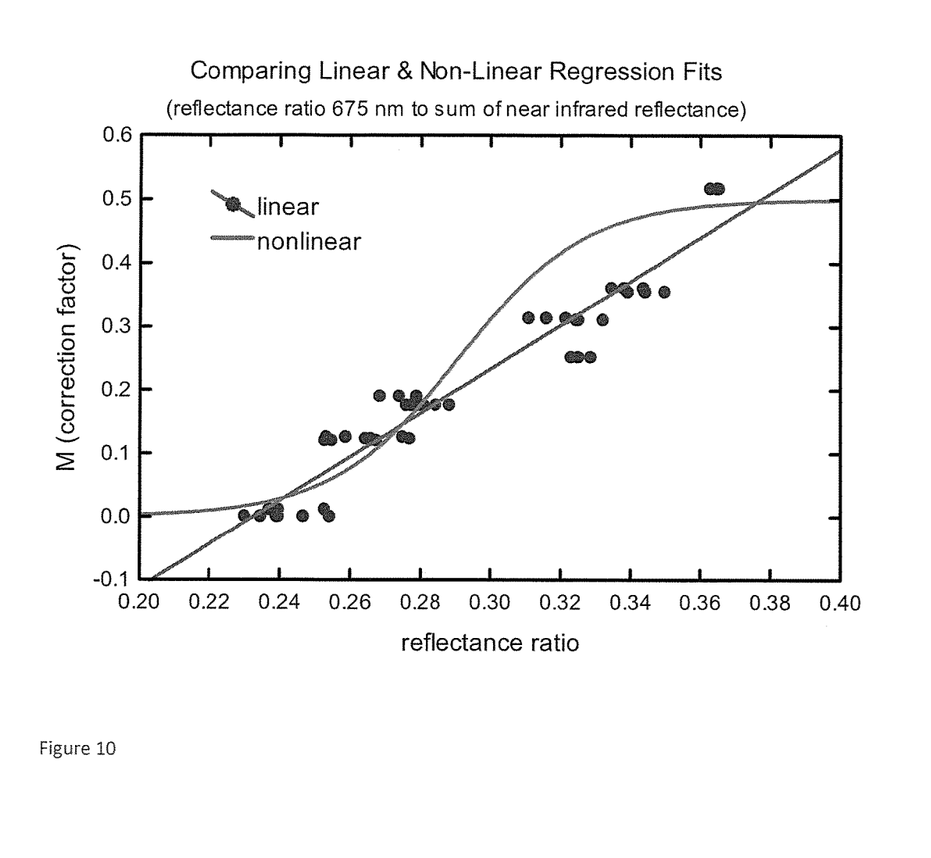
FIG. 10: Demonstrates that nonlinear functions, a logistic function, can be used to predict the melanin conversion factor M=(1−L/Lmax) based on the measured reflectance at one or more wavelengths in the near infrared.

While equations (5) and (6) define linear regression models, non-linear regression models such as exponential growth or hyperbolic tangent can also be used to provide adequate melanin compensation for these various approaches delineated above. FIG. 10 compares a linear fit to a nonlinear, logistic regression type fit to predict the melanin correction factor based on measuring the reflectance of skin at discrete wavelengths.

Figure 11:
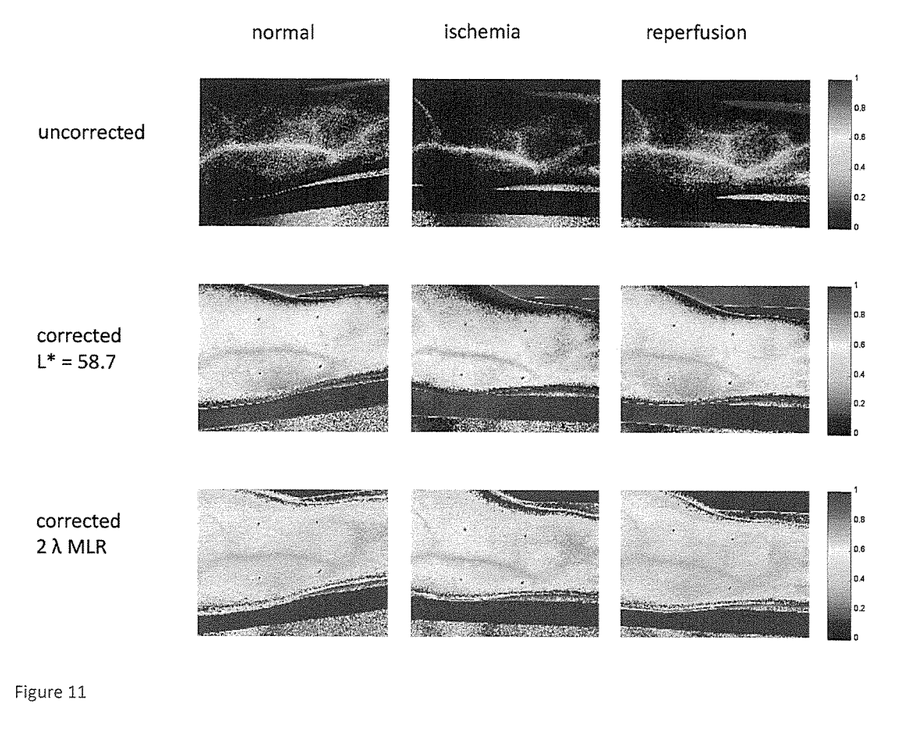

Oxygenation images computed from skin reflectance measured at 670, 735, 890 and 940 nm without using a melanin correction are compared in FIG. 11 to oxygenation images where the reflectance was first corrected for skin melanin. The two melanin correction procedures described herein are compared in rows 2 and 3 of FIG. 11. The former method requires prior knowledge of the lightness of skin, the L* value in the Lab colorspace; the latter method estimates the magnitude of the melanin correction directly from the series of reflectance images used to calculate the oxygenation image. This latter method enables a correction to be performed on a pixel-by-pixel basis.

In order to minimize the effect of varying hemoglobin and hemoglobin oxygenation on the melanin correction procedure, the regression model can be developed based on the reflectance measured at wavelengths where hemoglobin shows little differential absorption or where the oxygenated and deoxygenated forms of hemoglobin show equal absorption. These latter wavelengths are known as the isobestic points. However, more generally, the regression model can be constrained to minimize the influence of these covariates. One such approach is to consider that the reflectance measurements result in a data matrix, X, of the form, $$X = X_{mel} + X_{-mel} \quad (7)$$

where $X_{mel}$ captures the contributions from varying skin melanin and $X_{-mel}$ captures the contributions unrelated to melanin. A data filter can be developed that filters out all contributions unrelated to melanin. For example, $$F = I - (X_{-mel})^+ X_{-mel} \quad (8)$$

F is the projector onto the subspace orthogonal to the variations that are unrelated to melanin when $(X_{-mel})^+$ is the pseudo-inverse of $X_{-mel}$. There are a number of ways to estimate $X_{-mel}$. One such method is to explicitly include or add variations through imputation of known or expected covariates into the database. For example, data is collected from each subject in our database where the blood supply to the target tissue is manipulated. Thus changes in the reflectance are invoked that are not related to the melanin content of the skin. The within-subject variation of this study design provides an estimate of $X_{-mel}$ needed to design the filter.

$$\tilde{X}_{mel} = X - XFF^T \quad (9)$$

Figure 12:
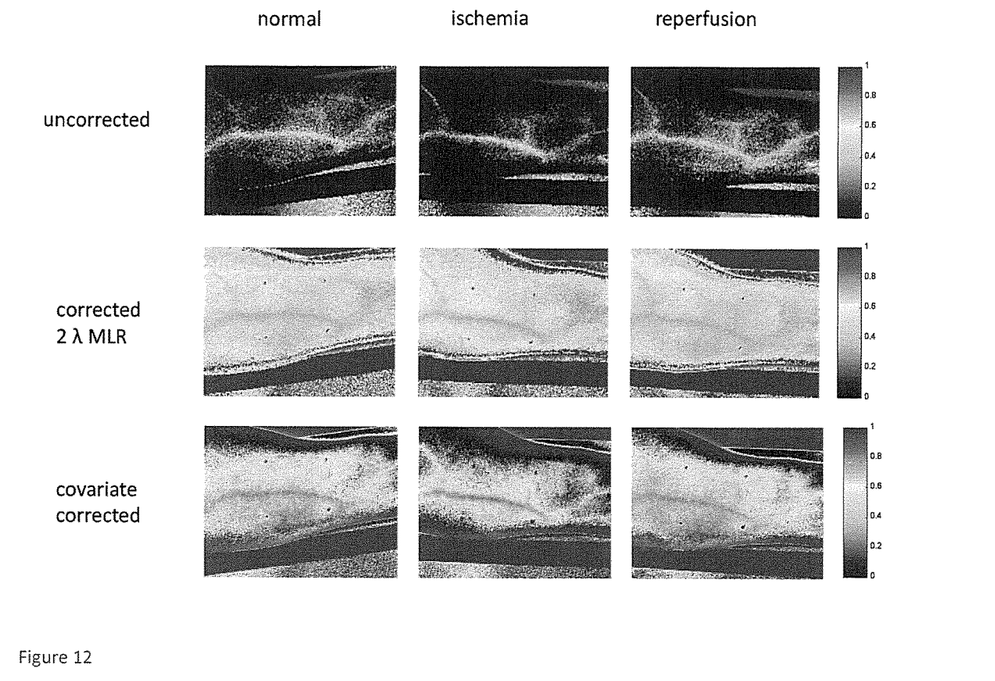

Oxygenation images computed from skin reflectance measured at 670, 735, 890 and 940 nm without using a melanin correction are compared in FIG. 12 to oxygenation images where the reflectance was first corrected for skin melanin without explicitly considering covariates and then when melanin was corrected accounting for non-melanin variations in the reflectance from the skin. The later method (row 3, FIG. 12) can better discriminate attenuation of skin reflectance arising from melanin compared to, for example, reflectance changes arising from changing tissue blood volume or oxygenation.

The regression model developed on a database of skin reflectance measurements with known L* skin color measures can be applied to convert the covariate corrected skin reflectance measurements made at the same K wavelengths used in the regression model. In those instances the L* value associated with the reflectance does not need to be known. Plugging the M correction term predicted by the regression model into equation 4 provides the wavelength dependent correction for melanin. Note that over a narrow wavelength range a linear approximation for $C(\lambda)$ can be used (see FIG. 1) to account for the wavelength dependence of the light absorption from melanin rather than equation (3.). However, more generally the nonlinear term reported in equation (3) can be used. Accounting for covariate induced changes in skin reflectance improves the contrast in oxygenation images taken when tissue is normally perfused compared to states where the blood supply to tissue is interrupted or attenuated.

The scope of the claims should not be limited by the preferred embodiments set forth in the examples, but should be given the broadest interpretation consistent with the description as a whole.

REFERENCES

1.) N. L. Whiteing. Skin assessment of patients at risk of pressure ulcers. Nursing Standard 24(10):40-44, 2009.
2.) P. Valisuo, I. Kaartinen, V. Tuchin and J. Alander. New closed-form approximation for skin chromophore mapping. J. Biomed. Opt. 16: 046012, 2010.
3.) L. Wang, S. L. Jacques and L. Zheng. MCML—Monte Carlo modeling of light transport in multi-layered tissues. Comput. Methods Programs Biomed. 47: 131, 1995.
4.) A. D. Kim. Transport theory for light propagation in biological tissue. J. Opt. Soc. Am. A., 21(5), 820-827, 2004.
5.) F. Martelli. ABC of near infrared photon migration in tissues: the diffusive regime of propagation, J. Near Infrared Spectrosc., 20(1): 29-42, 2012.
6.) I. L. Weatherall, B. D. Coombs, Skin Color Measurements in Terms of CIELAB Color Space Values, J. Investigative Dermatology 99, 468-473; 1992.
7.) S. Sachdeva; Fitzpatrick skin typing: Applications in dermatology. Indian J Dermatol 75(1): 93-96, 2009.
8.) A. Fullerton, T. Fischer, A. Lahti, K.-P. Wilhelm, H. Takiwaki and J. Serup. Guidelines for measurement of skin colour and erythema. A report from the Standardization Group of the European Society of Contact Dermatitis. Contact Dermatitis 35: 1-10, 1996.

The invention claimed is:

1. A method for compensating for melanin absorption during near-infrared imaging, visible imaging or near-infrared and visible imaging of concentration and distribution of biomolecules of interest in a tissue portion comprising:

determining skin color of the tissue portion, wherein the skin color is determined by measuring light reflected from the tissue portion at two or more wavelengths and using reflectance to calculate the skin color of the tissue portion;

determining a melanin correction factor from the skin color, wherein the correction for melanin absorption comprises multiplying absorption at each wavelength by the melanin correction factor and subtracting said absorption at each wavelength so as to subtract absorption due to melanin from the image; and correcting for melanin absorption at each wavelength used for imaging the tissue portion, thereby providing a corrected image of the tissue portion and the biomolecules of interest within the tissue portion, and displaying the corrected image of the tissue portion.

2. The method according to claim 1 wherein the subtraction is made at pixels of the image.

3. The method according to claim 1 wherein the skin color is calculated by a regression model.

4. The method according to claim 3 wherein the regression model is derived from a database of reflectance measurements from subjects with known skin color or skin melanin content.

5. The method according to claim 3 wherein the regression model is derived from the difference in the reflected at two or more wavelengths from a tissue portion to one or more prototype tissue portions with limited or extensive melanin.

6. The method according to claim 1 wherein the skin color is estimated from a color digital image of the tissue portion.

* * * * *